United States Patent
Berghmans et al.

(10) Patent No.: US 11,426,768 B2
(45) Date of Patent: Aug. 30, 2022

(54) SORTING APPARATUS

(71) Applicant: Optimum N.V., Kuringen (BE)

(72) Inventors: Paul Berghmans, Kuringen (BE); Jan De Jonghe, Kuringen (BE); Patrick Beyens, Kuringen (BE); Jannis Frederickx, Kuringen (BE)

(73) Assignee: Optimum N.V., Kuringen (BE)

( * ) Notice: Subject to any disclaimer, the term of this patent is extended or adjusted under 35 U.S.C. 154(b) by 0 days.

(21) Appl. No.: 16/574,341

(22) Filed: Sep. 18, 2019

(65) Prior Publication Data

US 2020/0139409 A1 May 7, 2020

(30) Foreign Application Priority Data

Sep. 18, 2018 (BE) .................................. 2018/0109

(51) Int. Cl.
  *B07C 5/342* (2006.01)
(52) U.S. Cl.
  CPC .................................. *B07C 5/3425* (2013.01)
(58) Field of Classification Search
  CPC ...... B07C 5/3425; B07C 5/342; G01N 21/85; G01N 2021/845; G01N 2021/8592; G01N 2021/8466
  See application file for complete search history.

(56) References Cited

U.S. PATENT DOCUMENTS

| 3,713,743 | A | 1/1973 | Simms |
| 4,634,881 | A | 1/1987 | Billion |
| 4,723,659 | A | 2/1988 | Billion |
| 6,507,400 | B1 | 6/2003 | Pina et al. |
| 6,864,970 | B1 | 3/2005 | Ruymen et al. |
| 9,395,346 | B2 * | 7/2016 | Walukas .............. A01K 45/007 |
| 2010/0290032 | A1 | 11/2010 | Bugge |
| 2010/0290040 | A1 | 11/2010 | Berghmans |
| 2014/0186874 | A1 | 7/2014 | Lu |

FOREIGN PATENT DOCUMENTS

| EP | 396737 A2 | 10/2004 |
| EP | 1332353 B1 | 12/2009 |
| WO | 83/04098 A1 | 11/1983 |
| WO | 98/31477 | 7/1998 |
| WO | 2014/013421 A1 | 1/2014 |

* cited by examiner

*Primary Examiner* — Michael McCullough
*Assistant Examiner* — Jessica L Burkman
(74) *Attorney, Agent, or Firm* — Browdy and Neimark, PLLC

(57) ABSTRACT

A method for sorting products and sorting apparatus with a flow of granular products moving in an inspection zone, in which a light beam is moved over the product flow to generate a reflected stream of light. At least one detector unit is provided to detect light reflected by the products to generate detection signals. This detector unit cooperates with a control unit to sort the products by these detection signals. The detector unit contains at least two sensors that are provided one after the other in the reflected stream of light so that a sensor is placed upstream of a downstream sensor. Each sensor detects a different part of the reflected stream of light.

19 Claims, 3 Drawing Sheets

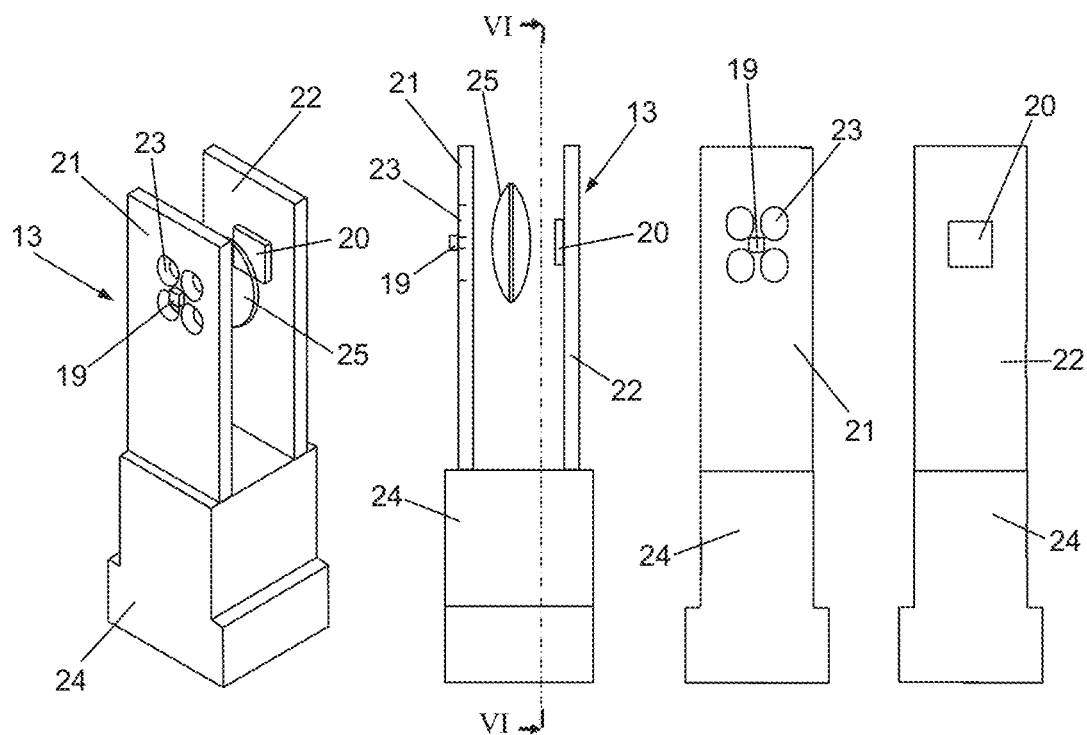
*Fig. 3*   *Fig. 4*   *Fig. 5*   *Fig. 6*
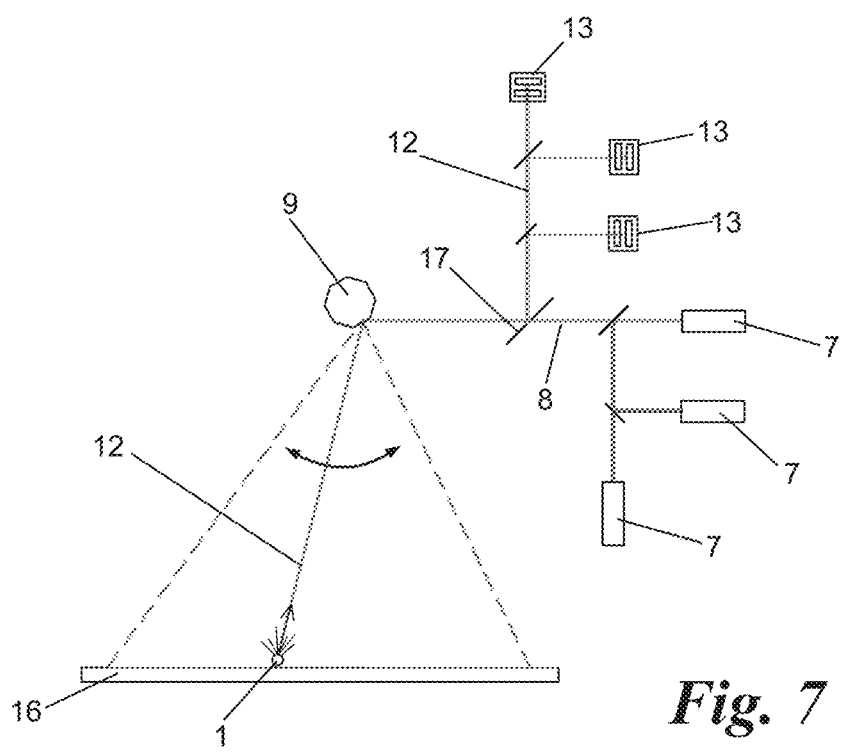
*Fig. 7*

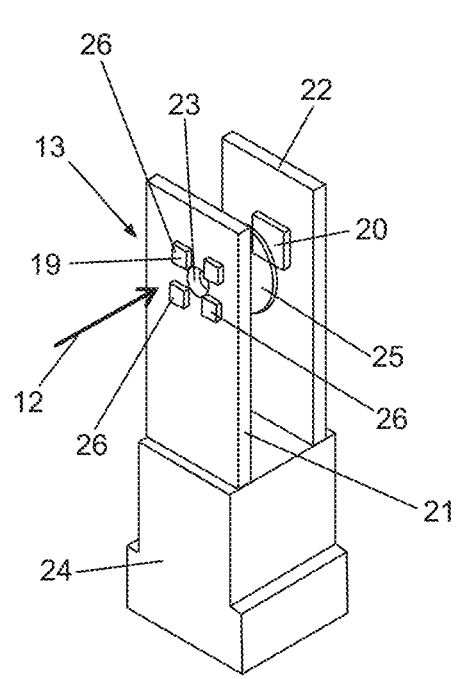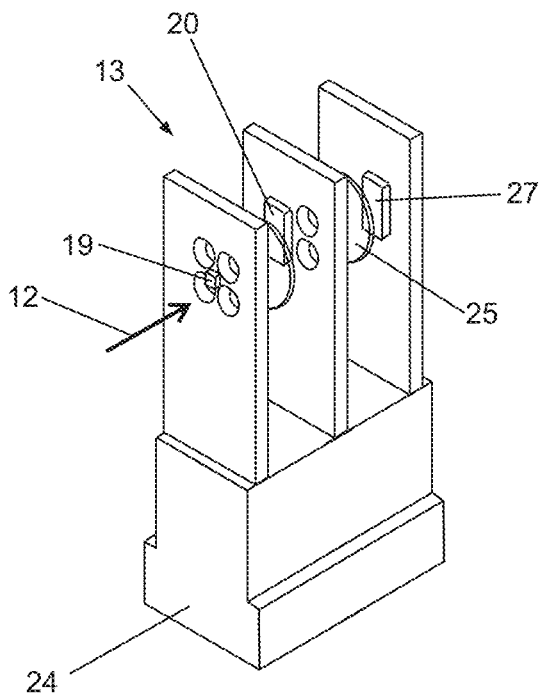
*Fig. 8*  *Fig. 9*
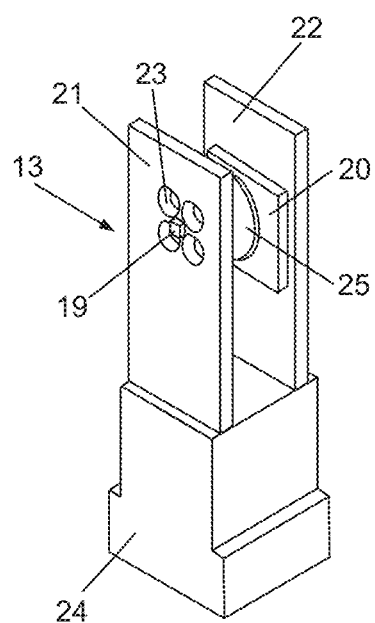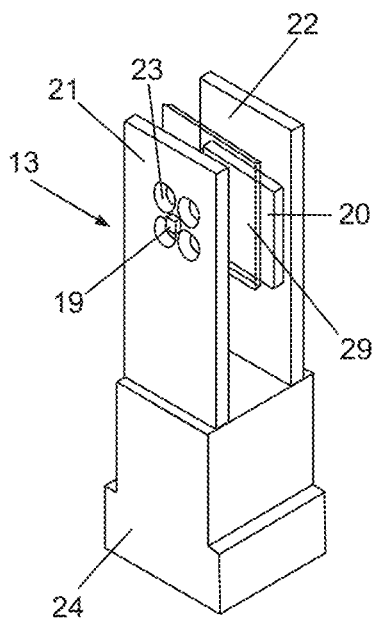
*Fig. 10*  *Fig. 11*

SORTING APPARATUS

The invention concerns a sorting machine with an inspection zone for detecting impurities or unwanted products in a flow of products moving through this inspection zone. In particular, this flow of products consists of loosely moving granular products. This sorting machine has at least one light source to generate a light beam, with means to move this beam almost transversely to the direction of movement of the product flow, so that almost all products are hit by the beam in the inspection zone in order to generate a reflected stream of light. Light from this light beam is directly reflected here by the products from an impact point of the light beam on the products, and this light is scattered and reflected from a zone around this impact point. At least one detector unit is provided to detect light reflected by the products in order to generate detection signals, wherein this detector unit works together with a control unit to use these detection signals to sort the products of the product flow.

According to the present state of the art, the reflected light beam is split into at least two different light beams by using, for example, a radiation divider. Each of these light beams is then led to an associated detector, wherein the intensity of directly reflected light is measured for one light beam, while the intensity of the scattered reflected light is determined for another light beam.

Such sorting machines are described, for example, in document U.S. Pat. No. 6,864,970 where a reflected laser beam is divided into two light beams by means of a beam splitter. In document U.S. Pat. No. 4,723,659, a mirror with a central aperture is used to divide the reflected light beam into a light beam containing mainly directly reflected light and a light beam consisting mainly of scattered reflected light.

When a reflected light beam is split into two different light beams by, for example, a beam splitter, two light beams are obtained whose light intensity is at the most half the light intensity of the original reflected light beam. This obviously has a negative impact on the measurement sensitivity and the accuracy of the sorting machine. In addition, both light beams have a different orientation, with the angle between the two light beams usually being about 90°. The latter ensures that means of dividing the reflected light beam into two different light beams, together with a sensor for each of the two light beams obtained, occupy relatively much space in the optical module of the sorting machine.

Document US 2010/0290040 describes a sorting machine with a detector that contains only one sensor for both the detection of directly reflected light and scattered reflected light. The manufacture of such a sensor is very complex and requires considerable investments. In addition, due to the extremely high cost of this type of detector, its use in sorting machines is not economically justified.

The invention aims to remedy these disadvantages by proposing a sorting machine in which a light beam is incident on each of the sensors while maintaining a high intensity on the one hand, while a compact arrangement can be achieved compared to the existing sorting machines on the other hand. This ensures that a more accurate signal can be generated by the sensors so that the flow of products can be sorted with a high degree of accuracy by means of a compact optical module.

To this aim, said detector unit contains at least two sensors which are provided one after the other in said reflected stream of light, in particular in the same optical path of the reflected stream of light, so that a sensor is positioned upstream of a sensor situated downstream, each sensor detecting a different part of the reflected stream of light.

Practically, said upstream sensor shields the downstream sensor from at least the reflected light that is incident on the upstream sensor.

According to a preferred embodiment of the sorting machine according to the invention, one of said sensors is provided to detect at least mainly directly reflected light, while another sensor is equipped with these sensors to detect at least mainly scattered reflected light.

Preferably, an optical element such as a lens is provided to make reflected light that is not detected by said upstream sensor enter said downstream sensor. This optical element is provided, for example, between the above-mentioned sensors. The optical element may be formed by a lens and is preferably a divergent lens.

According to an interesting embodiment of the sorting machine according to the invention, each of said sensors is mounted on an associated support wherein these supports are provided one after the other in said reflected stream of light, wherein a support of the upstream sensor has a recess so that reflected light passes through this recess on the downstream sensor.

According to an advantageous embodiment of the sorting machine according to the invention, the support of the upstream sensor comprises at least one recess for scattered reflected light from said stream of light. In this case, the upstream sensor is positioned in such a way that directly reflected light is incident on this sensor, while scattered reflected light passes through the recess in the downstream sensor.

According to an additional embodiment of the sorting machine according to the invention, an optical element located upstream of said detector unit is provided in order to distribute directly reflected light over virtually the entire surface of said upstream sensor of the detector unit. Such an optical element is, for example, formed by a lens.

The invention also concerns a method of detecting impurities or unwanted products in a flow of products moving according to a direction of movement through an inspection zone, wherein a beam of light is moved across this inspection zone in such a way that virtually all products are hit by the light beam in said inspection zone and a reflected stream of light is generated. The moving flow of products is preferably formed of discrete granular products. The light from this light beam is herein directly reflected by the products from an impact point of the light beam on the products and it is scattered from a zone around this impact point, wherein the light intensity reflected by the products is detected in order to generate detection signals to sort said products with the help of these detection signals.

This method is characterised in that in at least two detection positions in said stream of light, in particular in the same optical path, the light intensity is measured in different parts of said reflected stream of light, wherein one of these detection positions is located upstream in the stream of light with respect to a detection position located downstream.

Other particularities and advantages of the invention will become clear from the following description of a few specific embodiments of the sorting machine and the method according to the invention. This description is given as an example only and does not limit the scope of the claimed protection in any way; the reference figures used below refer to the accompanying figures.

FIG. 3 is a schematic view in perspective of a detector unit with an upstream and downstream sensor according to an interesting embodiment of the invention.

FIG. 4 is a schematic side view of the detector unit from FIG. 3.

FIG. 5 is a schematic front view of the detector unit from FIG. 3 with said upstream sensor.

FIG. 6 is a schematic cross-section of the detector unit according to plane VI-VI in FIG. 4, with said downstream sensor.

FIG. 7 is a schematic representation of a detection device of a sorting machine with three detector units according to the invention.

FIG. 8 is a schematic view in perspective of a detector unit according to an alternative embodiment of the invention.

FIG. 9 is a schematic view in perspective of an example of a detector unit according to the invention with three sensors.

FIG. 10 is a schematic view in perspective of a detector unit according to a particularly interesting embodiment of the invention.

FIG. 11 is a schematic view in perspective of a detector unit according to an alternative embodiment of the invention wherein an optical filter is provided between an upstream sensor and a downstream sensor.

In the different figures, the same reference figures refer to identical or similar elements.

The invention in general concerns a sorting machine to sort, preferably, granular products such as peas, nuts, raisins, potatoes, frozen products, etc. To this end, these products are moved as a wide product flow through a detection device where a concentrated beam of light hits the product flow in order to detect any unwanted products and remove them from the product flow. The products that are moved in the product flow along the detection device preferably show the smallest possible dispersion in a direction transverse to the direction of movement of the products. Thus, the thickness of the product flow in the place where the light beam hits it is virtually equal to the thickness of a single product.

By sorting is meant in particular in this description the removal of unwanted products from a product flow such as extraneous matter, impurities or products which do not meet the required quality requirements, etc. Said light beam is formed, for example, by one or more laser beams.

Figure 1:
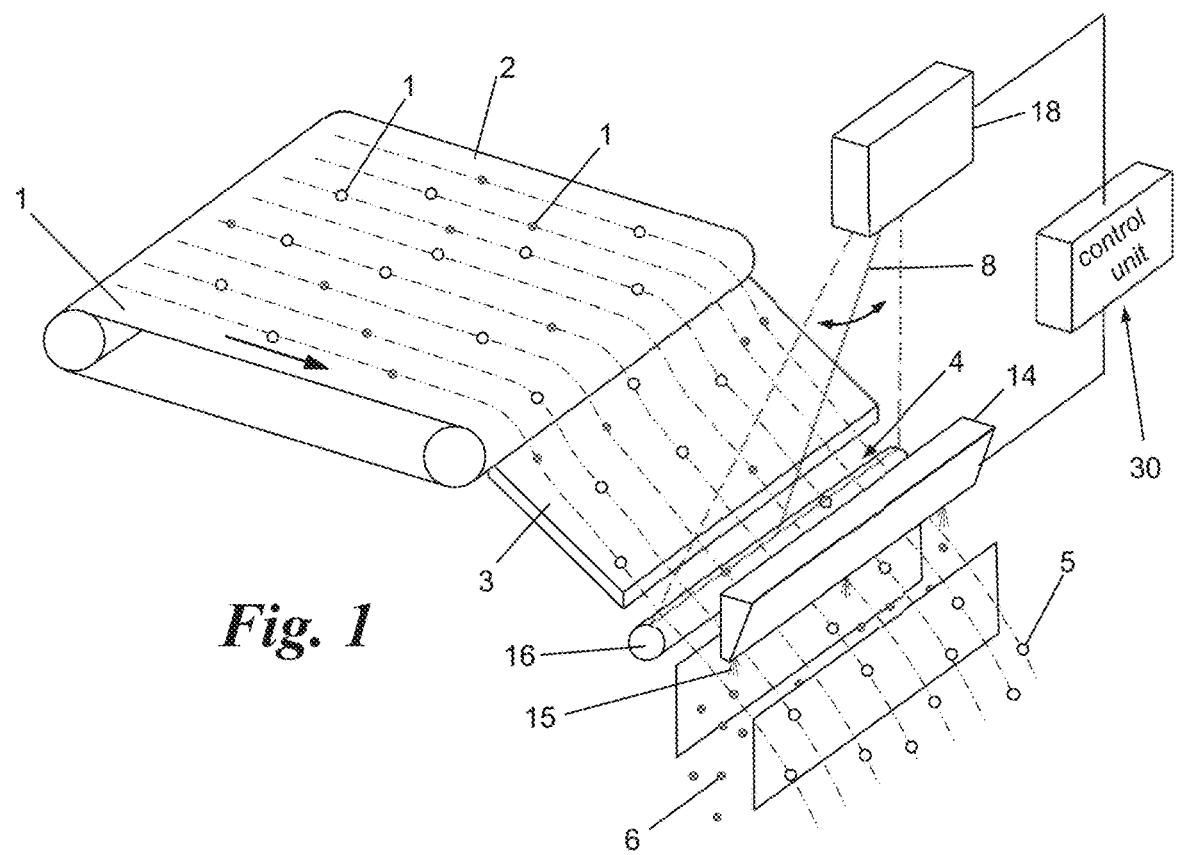
FIG. 1 is a schematic view in perspective of a sorting machine with a detection device and a removal device according to the invention.

A first embodiment of such a sorting machine is shown in FIG. 1. The products 1 to be sorted are placed on a conveyor belt 2 where the products 1 are moved as a product flow at a speed determined by the conveyor belt's travel speed 2 towards an inclined plane 3. The products 1 then move down this inclined plane 3 under the influence of gravity so that the products 1 leave the inclined plane 3 as a broad flow with a thickness of virtually one product 1 and move through an inspection zone 4 of the sorting machine.

Alternative ways of feeding the products 1 through the inspection zone 4 can of course also be provided. For example, it is possible that the inclined plane 3, as shown in FIG. 1, is not present. In this case, the products 1 are thrown off the conveyor belt 2 at a sufficient speed to move them in free flight through the inspection zone 4 at an almost homogeneous speed. This type of feeding of products to the inspection zone 4 is shown for example in FIG. 1 of documents U.S. Pat. No. 4,723,659 or 4,634,881.

According to yet another way of feeding the products 1 to the inspection zone 4, they are made to move in freefall through the inspection zone 4. The products 1 are fed here, for example, by means of a vibrating table to a curved, or possibly straight plate with a surface approaching a fall parabola of the products 1. When leaving the plate, the products 1 move through the inspection zone 4 in a single layer at an almost homogeneous speed. This example is described for example in document WO 98/31477 or WO 2014/013421.

Figure 2:
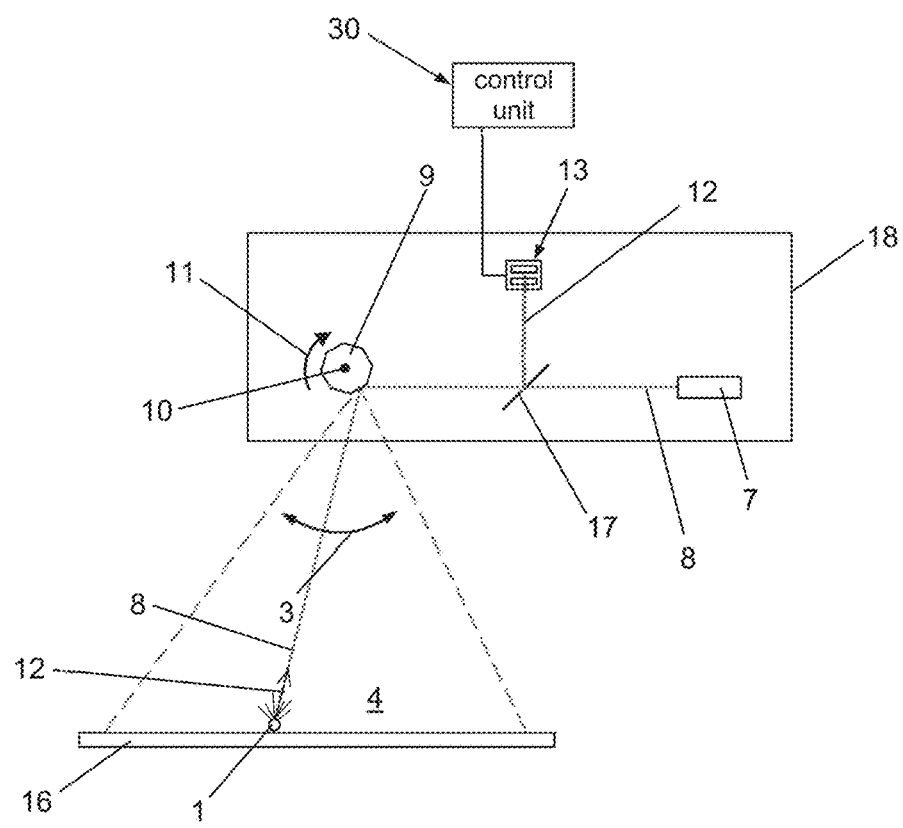
FIG. 2 is a schematic representation of a detection device of a sorting machine according to the invention.

In the inspection zone 4, each product 1 is scanned by means of a detection device 18 and it is checked whether a product 1 is a desired product 5 or an unwanted product 6. As shown in FIG. 2, this detection device 18 contains at least one light source 7 to generate a light beam 8, and means are provided to move this light beam 8 virtually transversely to the direction of movement of the product flow so that nearly all products 1 are hit by the light beam 8 in the inspection zone 4 in said inspection zone 4.

Said means for moving the light beam 8 include, for example, a so-called polygon mirror 9 which is subjected to a rotational movement around its central axis 10, as indicated by arrow 11. In particular, such a polygon mirror 9 is preferably formed by a straight prism with a regular polygon as its base and with rectangular reflecting lateral faces. When the light beam 8 hits the polygon mirror 9 in a direction perpendicular to its central axis, due to the rotation of the polygon mirror 9, the light beam 8 will scan over the entire width of the product flow in the inspection zone 4. The light beam 8 is moved almost transversely to the direction of movement of the product flow so that almost all products 1 are hit by the light beam 8 in said inspection zone 4. The light beam 8 is incident on the products 1 in the inspection zone 4 and is reflected by them, so that a reflected stream of light 12 is generated.

The light source 7 preferably allows to generate a highly concentrated light beam 8 and includes, for example, one or more laser sources or, for example, a super continuous light source. Thus, the incident light beam comprises, for example, one or more laser beams. Also the wavelength of the incident light beam 8 can be selected according to the nature and type of the products to be sorted. For example, this light beam 8 may contain IR light, NIR, UV light or visible light. The light beam 8 may possibly consist mainly of coherent light.

When the light beam 8 hits a product 1, it will be reflected directly from the impact point of the light beam 8 on the product 1 on the one hand, and it will be reflected in a scattered manner from a zone around this impact point due to the scattering of the light from the light beam 8 in the product 1 on the other hand.

The detection device 18 also contains at least one detector unit 13 to detect the light reflected by the products 1. Sensors of the detector unit 13 generate detection signals here as a function of the measured reflected stream of light 12. The detector unit 13 works in conjunction with a control unit 30 to sort the products 1 by means of the detection signals. For this purpose, downstream of the inspection zone 4, a removal device 14 is provided that includes, for example, a row of compressed air valves extending across the entire width of the product flow. If the presence of an unwanted product 6 is thus detected in the product flow by means of the detector unit 13, the removal device 14 will remove this product 6 from the product flow. As shown in FIG. 1, a compressed air valve of the removal device 14 is activated by the control unit 30 to this end to create a short airflow 15 that blows the unwanted product 6 out of the product flow.

The detection device 18 may be possibly also equipped with a background element 16 in the form of a tube, whose colour and other optical properties correspond, for example, to those of the desired products in the product flow to be sorted. This ensures that the removal device 14 is not activated when the light beam 8 hits the background element 16 instead of a product 1 to be sorted. The background element 16 is thus elongated and extends transversely to the direction of movement of the product flow and is almost parallel to the latter. The products 1 therefore move between the background element 16 and the polygon mirror 9.

When the light beam 8 hits an unwanted product 6, the quantity of directly reflected or scattered light will be different from that for a desired product 5. Thus, this directly and/or scattered reflected light is detected by the detector unit 13 in order to distinguish unwanted products 6 from desired products 5.

The directly reflected and scattered reflected light together form the reflected light beam 12 that is directed to the detector unit 13. The path of the incident light beam 8 and that of the reflected light beam 12 coincide almost up to a beam separator 17 that is provided between the light source 7 and the polygon mirror 9. The beam separator 17 separates the reflected light beam 12 almost entirely from the light beam 8 incident on the products 1. Such a beam separator 17 can, for example, be formed by a mirror with a central aperture, as described in document U.S. Pat. No. 4,634,881, or it can separate the incident light beam 8 and the reflected light beam 12 on the basis of the polarisation of these light beams as described in document EP 1 332 353.

FIGS. 3 to 6 schematically show an interesting embodiment of a detector unit 13 according to the invention. This detector unit 13 contains two sensors 19 and 20 that allow to measure the intensity of the light entering it and to thus generate a corresponding detection signal. These sensors 19 and 20 are located, one after the other, in the path of the reflected stream of light 12. Thus, a first sensor 19 is placed upstream with respect to a downstream sensor 20.

On each of these sensors 19 and 20, a different part of the reflected light beam 12 is incident so that, consequently, each sensor detects a different part of the light beam 12 reflected by the products 1. To this end, for example, a part of the downstream sensor 20 can be shielded from the light beam 12, while, in addition, the upstream sensor 19 only covers a part of the cross-sectional area of the light beam 12.

In the example shown in FIGS. 3 to 6, the upstream sensor 19 shields the downstream sensor 20 from a part of the reflected light. In particular, the field of view of the downstream sensor 20 is at least shielded from light incident on the upstream sensor 19.

In this specific example, it is ensured, for example, that light directly reflected by the products 1 is incident at least partially on the upstream sensor 19. For this purpose, the reflected light beam 12 is preferably incident on the detector unit 13 in such a way that the upstream sensor 19 is situated virtually in the middle of the light beam 12. The diameter of the sensor 19 should preferably correspond then to the diameter of the part of the light beam 12 that contains directly reflected light from the products 1.

The light from the reflected light beam 12, which is not incident on the upstream sensor 19, is at least partially incident on the sensor 20 which is located downstream in the path of the light beam 12. Thus, the upstream sensor 19 detects at least mainly directly reflected light, while the downstream sensor 20 detects at least mainly scattered reflected light.

Each of said sensors 19 and 20 is mounted on a corresponding support 21, 22 respectively. These supports 21 and 22 are provided one after the other in the path of the reflected stream of light 12. The support 21 of the upstream sensor 19 herein has at least one recess 23 so that reflected light can pass through this recess 23 onto the downstream sensor 20. The recess 23 preferably connects to the upstream sensor 19 or at a short distance from the latter. Due to structural requirements, several recesses 23 are provided, for example, so that the presence of ribs between two adjacent recesses 23 allows the sensor 19 to be sufficiently firmly secured to the corresponding support 21.

In general, the supports 21 and 22 can be formed by a so-called Printed Circuit Board (PCB) on which the relevant sensor is provided. These recesses 23 are then provided in the printed circuit board, making sure that no electronic components or wires are present at the location of these recesses 23.

As shown in FIGS. 3 to 6, these supports 21 and 22 are formed, for example, by plates that preferably extend parallel to each other. Said sensors 19 and 20 are then mounted on this plate, possibly together with associated electronic circuits.

According to an interesting embodiment of the invention, the supports 21 and 22 are provided on a common socle 24. This simplifies the accurate installation of the detector unit 13 in the detection device 18 of the sorting machine. In addition, it is ensured that, for the same detector unit 13, both supports 21 and 22 with corresponding sensors 19 and 20 and recesses 23 are aligned to each other.

According to an interesting embodiment of a detector unit 13 according to the invention, the support 21 of the upstream sensor 19 comprises at least a recess 23 for scattered reflected light from the reflected stream of light 12. This upstream sensor 19 is positioned in such a way here that directly reflected light is incident on this sensor 19, while scattered reflected light passing through the recess 23 is incident on the downstream sensor 20.

According to an alternative embodiment of the detector unit 13 according to the invention, the support 21 of the upstream sensor 19 has a recess 23 for directly reflected light from the reflected stream of light 12. This sensor 19 is positioned in such a way with respect to the reflected stream of light 12 that scattered reflected light is incident on this sensor 19. The directly reflected light then preferably passes through the recess 23 onto a downstream sensor 20. Such an embodiment of the detector unit 13 is shown in FIG. 8. However, the sensor 19 herein includes four identical sensors 26 that are distributed around the recess 23. It goes without saying that this number of sensors 26 may be larger or smaller than four.

According to a variant of the above embodiments, two or more sensors 19, 20 respectively are provided, for example, located upstream or downstream. A different part of the reflected stream of light 12 can be incident on each of the sensors. For example, when these sensors 19 or 20 are located in different quadrants of a circle, the detection of the light intensity by the sensors in the different quadrants allows to verify or adjust the alignment of the reflected light beam.

In addition, a lens 25 may possibly be provided which makes reflected light that is not detected by the upstream sensor 19 incident on the downstream sensor 20. Thus, for example, it is not required that the surface of the downstream sensor 20 corresponds to the surface that is covered by said one or more recesses 23. Thus, the surface area of the downstream sensor 20 may be slightly smaller, for example, than the surface area covered by the recesses 23, or this sensor 20 may, for example, extend at least partially behind the upstream sensor 19 in the path of the reflected stream of light 12. FIGS. 3 and 4 schematically show the presence of such a lens 25.

In general, in an interesting way, between an upstream sensor 19 and a following downstream sensor 20, an optical element, in particular a lens 25, is preferably provided which allows light that passes beyond the upstream sensor 19 to be incident on as large a surface area as possible of the downstream sensor 20.

In particular, the measurement sensitivity of the sensor 19 or 20 increases as its surface area increases. Thus, for example, it is decided to choose the surface area of the downstream sensor 20 larger than the surface area of the cross-section of the light beam that passes through the upstream sensor 19, as shown schematically in FIG. 10. In this case, the surface area of the sensor 20 is therefore preferably larger than the surface area covered by the recesses 23 in the support 21 of the upstream sensor 19. However, according to another embodiment, the surface area of the downstream sensor 20 may be less than or equal to the surface covered by the recesses 23 in the support 21 of the upstream sensor 19.

An optical element is thus provided between both sensors 19 and 20 which ensures that the light beam is spread over as large a part as possible of the surface of the downstream sensor 20. Such an optical element is formed, for example, by a diverging lens 25. In particular, this optical element allows reflected light to also hit the part of the downstream sensor 20 that is shielded by the upstream sensor 19 or by the support 21 on which it is provided.

The lens 25 is provided between both sensors 19 and 20, but in some cases, it may be interesting to provide this lens 25 upstream of the upstream sensor 19.

The presence of an optical element such as a lens 25, upstream of a sensor 19 or 20, allows light that should be incident on this sensor 19 or 20 to spread, for example, over virtually the entire surface thereof.

Furthermore, it is also possible to provide an optical filter 29 in the detector unit 13, between the upstream sensor 19 and at least one downstream sensor 20, as is illustrated in FIG. 11. This filter 29 allows light of a certain wavelength to be blocked or transmitted, for example, in such a way that products can be sorted according to the properties associated with the filtered wavelength.

FIG. 7 shows a special embodiment of a sorting machine according to the invention. In this sorting machine, the detection device is equipped with three light sources 7, each generating a corresponding light beam 8. These light beams 8 are led to the polygon mirror 9 so that they are moved over the width of the product flow along the same optical path, thus forming a single light beam with light from different light sources 7.

Each light source 7 thus generates, for example, a laser beam with a different wavelength. After the light beam 8 has hit a product, it is reflected directly and/or scattered by this product. The reflected light beam 12 is then led via the polygon mirror 9 to various detector units 13. This involves splitting the reflected light beam into the various constituent light beams so that each detector unit 13 preferably receives light coming from a corresponding light source 7.

FIG. 9 shows yet another example of a detector unit 13 according to the invention. This detector unit 13 contains three sensors 19, 20 and 27, wherein each of these sensors 19, 20 and 27 detects a different part of the reflected stream of light 12. The sensor 19 is located upstream in the stream of light 12 with respect to the sensor 20, while the sensor 27 is positioned downstream with respect to the latter sensor 20. Each sensor shields light from the stream of light 12 for the downstream sensor(s).

Furthermore, each sensor 19, 20 and 27 in this embodiment is mounted on a corresponding support 21, 22 and 28 respectively. The upstream supports 21 and 22 have 23 recesses through which light can pass onto at least one of the rear sensors 20 or 27.

It goes without saying that the detector unit 13 may also contain more than two or three successive sensors downstream in the stream of light 12, the corresponding upstream supports having the necessary recesses 23 so that light from the stream of light 12 can reach the downstream sensors.

Of course, the invention is not limited to the embodiments of the sorting machine and the method for sorting products described above and shown in the attached figures. For example, the conveyor belt 2 and/or the inclined plane 3 can be replaced by another feeding device. This may include, for example, a vibrating table followed by a downwards inclined plate as described in EP 0 952 895. In this case, the products to be sorted in the product flow move in free fall through the inspection zone 4.

The invention claimed is:

1. A sorting machine with an inspection zone for the detection of impurities or unwanted products in a flow of granular products moving through said inspection zone with at least one light source for generating a light beam, wherein means are provided to move said light beam transversely to the direction of movement of the product flow so that at least some of the products are hit by the light beam in said inspection zone to generate a reflected stream of light, wherein the light from said light beam is directly reflected by the products from an impact point of the light beam on the products and is reflected as scattered from a zone around said impact point,
   wherein at least one detector unit is provided to detect light reflected by the products to generate detection signals, wherein said detector unit cooperates with a control unit of the sorting machine to sort the products in accordance with said detection signals,
   wherein said detector unit contains at least two sensors that are provided one after the other in said reflected stream of light so that an upstream sensor is placed upstream of a downstream sensor, wherein each sensor detects a different part of the reflected stream of light,
   said sorting machine comprising a lens which makes reflected light that is not detected by said upstream sensor incident on said downstream sensor.

2. The sorting machine according to claim 1, wherein said upstream sensor shields the downstream sensor from at least the reflected light that is incident on the upstream sensor.

3. The sorting machine according to claim 1, wherein one of said sensors detects directly reflected light, while another sensor of said sensors detects at least mainly scattered reflected light.

4. The sorting machine according to claim 1, wherein said lens is provided between said sensors.

5. The sorting machine according to claim 1, wherein said lens is a divergent lens, and wherein said downstream sensor has a surface area that is larger than the surface area of the cross-section of the reflected light beam passing the upstream sensor.

6. The sorting machine according to claim 1, wherein each of said sensors is mounted on a corresponding support, wherein said supports are provided one after the other in said reflected stream of light, wherein a support of the upstream sensor has a recess so that reflected light passes through said recess on the downstream sensor.

7. The sorting machine according to claim 6, wherein said support of the upstream sensor contains at least one recess for scattered reflected light from said stream of light, wherein said upstream sensor is positioned such that directly reflected light is incident on said upstream sensor, while scattered reflected light passes through said recess on the downstream sensor.

8. The sorting machine according to claim 6, wherein said support of the upstream sensor contains at least a recess for directly reflected light from said stream of light, wherein said upstream sensor is positioned such that scattered reflected light is incident on said upstream sensor.

9. The sorting machine according to claim 6, wherein the support of said downstream sensor contains one or more additional sensors, wherein a different part of said stream of light is incident on each sensor.

10. The sorting machine according to claim 1, further comprising a lens disposed upstream of said detector unit to distribute directly reflected light over virtually the entire surface of said upstream sensor of the detector unit.

11. A sorting machine with an inspection zone for the detection of impurities or unwanted products in a flow of granular products moving through said inspection zone with at least one light source for generating a light beam, wherein means are provided to move said light beam transversely to the direction of movement of the product flow so that at least some of the products are hit by the light beam in said inspection zone to generate a reflected stream of light, wherein the light from said light beam is directly reflected by the products from an impact point of the light beam on the products and is reflected as scattered from a zone around said impact point,
wherein at least one detector unit is provided to detect light reflected by the products to generate detection signals, wherein said detector unit cooperates with a control unit of the sorting machine to sort the products in accordance with said detection signals, wherein
said detector unit contains at least two sensors that are provided one after the other in said reflected stream of light so that an upstream sensor is placed upstream of a downstream sensor, wherein each sensor detects a different part of the reflected stream of light,
wherein an optical filter is provided between said upstream sensor and at least one downstream sensor, through which reflected light that is not detected by said upstream sensor is incident on the downstream sensor.

12. The sorting machine according to claim 11, further comprising a lens disposed upstream of said detector unit to distribute directly reflected light over virtually the entire surface of said upstream sensor of the detector unit.

13. A method for detecting impurities or unwanted products in a flow of granular products moving through an inspection zone, wherein a light beam is moved over said inspection zone in such a way that at least some of the products are hit by the light beam in said inspection zone so that a reflected stream of light is generated, wherein the light from said light beam is directly reflected by the products from an impact point of the light beam on the products and is reflected as scattered from a zone around this impact point,
wherein light intensity reflected by the products is detected to generate detection signals to sort said products in accordance with said detection signals,
wherein at least in two detection positions in said reflected stream of light the light intensity is measured in different parts of said reflected stream of light, wherein one of said detection positions is situated upstream in the stream of light with respect to a downstream detection position,
wherein a lens provided between said upstream detection position and said downstream detection position to make reflected light that is not detected in said upstream detection position incident on said downstream detection position.

14. The method according to claim 13, wherein intensity of directly reflected light is detected in the reflected stream of light at the first of said detection positions, whereas intensity of scattered reflected light is detected at the second position.

15. The method according to claim 13, wherein said downstream detection position is shielded from light from the reflected stream of light whose intensity is measured at said upstream detection position.

16. The method according to claim 13 wherein at least a part of the light from the stream of light, whose intensity is not measured at said upstream detection position, is diverted to a sensor provided at said downstream measuring position to generate detection signals.

17. The method according to claim 13, wherein the intensity of the reflected light is measured with a sensor at said upstream measuring position to generate detection signals.

18. The method according to claim 13, wherein said detection signals are used to trigger a removal device to remove impurities or unwanted products from said flow of products.

19. A sorting machine with an inspection zone for the detection of impurities or unwanted products in a flow of granular products moving through said inspection zone, said sorting machine comprising:
at least one light source for generating a light beam,
a mirror configured to move said light beam transversely to the direction of movement of the product flow so that at least some of the products are hit by the light beam in said inspection zone to generate a reflected stream of light, wherein the light from said light beam is directly reflected by the products from an impact point of the light beam on the products and is reflected as scattered from a zone around said impact point,
at least one detector unit to detect light reflected by the products to generate detection signals,
a control unit configured to cooperate with said detector unit to sort the products in accordance with said detection signals,
wherein said detector unit contains at least two sensors disposed one after another in said reflected stream of light so that an upstream sensor is placed upstream of a downstream sensor, wherein each sensor detects a different part of the reflected stream of light, and
wherein said detector unit comprises a lens which makes reflected light that is not detected by said upstream sensor incident on said downstream sensor.

* * * * *